US00PP33797P2

(12) United States Plant Patent
Boxriker

(10) Patent No.: US PP33,797 P2
(45) Date of Patent: Dec. 28, 2021

(54) ***OSTEOSPERMUM* PLANT NAMED 'KLEOE20559'**

(50) Latin Name: ***Osteospermum ecklonis* Norl.**
Varietal Denomination: KLEOE20559

(71) Applicant: Klemm+Sohn GmbH & Co. KG, Stuttgart (DE)

(72) Inventor: Maike Boxriker, Schwäbisch Gmünd (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/331,100

(22) Filed: May 26, 2021

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 6/148; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Osteospermum* plant particularly distinguished by flowers having a compact and upright plant habit and purple ray florets with light-pink centers, is disclosed.

1 Drawing Sheet

Genus and species: *Osteospermum ecklonis* Norl.
Variety denomination: 'KLEOE20559'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE20559'. 'KLEOE20559' originated from a cross-pollination conducted in Summer 2016 in Nairobi, Kenya between the proprietary female *Osteospermum* variety 'KLEOE14235' (U.S. Plant Pat. No. 27,268) and the commercial male *Osteospermum* variety MARGARITA 'Pink Flair' (patent status unknown).

The seeds from the cross were sown and plants were grown in a greenhouse for evaluation, where an individual plant designated 'KLEOE20559' was selected from the group of plants in May 2017 in Stuttgart, Germany. In September 2017 in Stuttgart, Germany, 'KLEOE20559' was first vegetatively propagated by vegetative terminal cuttings. 'KLEOE20559' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. A compact and upright plant habit; and
2. Purple ray florets with light-pink centers.

DESCRIPTION OF THE PHOTOGRAPH

This new *Osteospermum* plant is illustrated by the accompanying photograph which shows a close-up the foliage, buds, and mature flower.

The photograph is of a 12-week-old plant grown in a greenhouse in Stuttgart, Germany in February 2020. The colors shown are as true as can be reasonably obtained by conventional photographic procedures.

DESCRIPTION OF THE NEW VARIETY

The following detailed descriptions set forth the distinctive characteristics of 'KLEOE20559'. The data which define these characteristics were collected in Latina, Italy in March 2021 on plants that were potted in week 42 of 2020. Color references are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis.*
- *Common.*—*Osteospermum.*
- *Designation.*—'KLEOE20559'.

Parentage:
- *Female parent.*—The proprietary *Osteospermum* variety 'KLEOE14235' (U.S. Plant Pat. No. 27,268).
- *Male parent.*—The male *Osteospermum* variety MARGARITA 'Pink Flair' (patent status unknown).

Plant:
- *Form and habit.*—Herbaceous perennial but usually cultivated as an annual; not frost resistant.
- *Growth habit.*—Compact and upright.
- *Branching habit.*—Upright.
- *Height (from top of soil, including inflorescence).*—17.0 cm. Width (including inflorescences): 18.0 cm. Propagation: Vegetative terminal cuttings. Time to produce a finished flowering plant: 9 weeks. Time to initiate and develop roots: 4 weeks. Root description: Fine, white RHS 156D.

Stems:
- *Total number of branches per plant (calculated at the base of the plant).*—5.

*Length.*—17.0 cm.
*Diameter.*—0.5 cm.
*Internode length.*—1.8 cm.
*Color.*—RHS 145A (Yellow-Green).
*Texture.*—Smooth.
*Anthocyanin.*—Present, at apex of stems RHS N77A (Purple).

Leaves:
*Arrangement.*—Alternate.
*Shape.*—Obovate.
*Apex.*—Acute.
*Base.*—Acute.
*Margin.*—Serrate.
*Immature color.*—Upper surface: RHS N137A (Green). Lower surface: RHS 137B (Green).
*Mature color.*—Upper surface: RHS N137A (Green). Lower surface: RHS 137C (Green).
*Length.*—6.5 cm.
*Width.*—3.6 cm.
*Texture and appearance.*—Upper surface: Leathery. Lower surface: Leathery with fine hairs.
*Petioles.*—Absent.
*Venation pattern.*—Pinnate.
*Venation color.*—Upper surface: RHS N144C (Yellow-Green). Lower surface: RHS 144D (Yellow-Green).

Flower buds:
*Shape.*—Round-ovoid.
*Apex.*—Acute.
*Length.*—1.1 cm.
*Diameter.*—1.1 cm.
*Color* (*at tight bud just before the ray florets unfold*).—RHS 144B (Yellow-Green).
*Texture.*—Smooth.

Inflorescence:
*Type.*—Composite, single.
*Blooming habit.*—Upright with slightly longer flower stems.
*Quantity of inflorescences per plant.*—21 open flowers per plant.
*Lastingness of the inflorescences on the plant.*—10 to 15 days.
*Fragrance.*—Slightly present; fresh, sweet.
*Inflorescence diameter.*—6.8 cm.
*Inflorescence depth.*—1.5 cm.
*Disc diameter.*—1.5 cm.

Disc floret:
*Quantity per inflorescence.*—About 100.
*Shape.*—Tubular.
*Tube color* (*closed and mature*).—RHS 163A (Greyed-Orange).
*Length.*—0.2 cm.
*Diameter* (*at apex*).—0.1 cm.
*Apex.*—Acute.
*Apex color.*—RHS 79A (Purple).
*Base.*—Acute.
*Base color.*—RHS 145A (Yellow-Green).
*Margin.*—Entire.

Ray floret:
*Quantity per inflorescence.*—26.
*Shape.*—Oblanceolate.
*Color.*—Upper surface: RHS 77B (Purple) with RHS 69B (Red-Purple) centers. Lower surface: RHS N77D (Purple).
*Length.*—2.8 cm.
*Width.*—1.0 cm.
*Apex.*—Acute.
*Base.*—Acute.
*Margin.*—Entire.
*Texture* (*upper and lower surfaces*).—Smooth.
*Peduncle.*—Length: 5.5 cm. Diameter: 0.2 cm. Texture: Smooth with hairs. Color: RHS 145B (Yellow-Green).

Phyllaries:
*Texture.*—Smooth with hairs.
*Color.*—RHS 144A (Yellow-Green).
*Arrangement.*—Single.
*Observed quantity per plant.*—23.
*Shape.*—Lanceolate.
*Color* (*both the upper and lower surfaces*).—RHS 144A (Yellow-Green).
*Length.*—0.9 cm.
*Width.*—0.2 cm.
*Apex.*—Entire.
*Base.*—Acute.
*Margin.*—Entire.
*Texture.*—Upper surface: Smooth with fine hairs. Lower surface: Smooth.

Reproductive organs:
*Androecium.*—Location: On disc and ray floret.
*Stamens.*—Quantity: 50-100. Shape: Filamentous. Filament length: 0.3 cm. Filament diameter: Less than 0.1 cm. Anther: Shape: Lanceolate. Color: RHS 79A (Purple). Length: Less than 0.1 cm. Diameter: Less than 0.1 cm. Pollen: Color: RHS 17A (Yellow-Orange). Amount: Moderate.
*Gynoecium.*—Location: On the base of the ray florets.
*Pistils.*—Number: 50 to 100. Length: 0.5 cm. Diameter: Less than 0.1 cm.
*Stigma.*—Color: RHS N7A7 (Purple). Shape: Filamentous. Length: 0.1 cm. Diameter: Less than 0.1 cm.
*Style.*—Color: RHS N77C (Purple). Length: 0.1 cm. Diameter: Less than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE20559' is a distinct variety of *Osteospermum* and is distinguished from its parents as described in Table 1.

TABLE 1

Comparison with Parental Lines

| Characteristic | 'KLEOE20559' | Female Parent 'KLEOE14235' | Male Parent MARGARITA 'Pink Flair' |
|---|---|---|---|
| Vigor | Compact | Semi-vigorous | Semi-vigorous |
| Plant size (height and width) | 17.0 cm and 18.0 cm | 30.0 cm and 25.0 cm | Between 25.4 cm and 35.6 cm for height and width |

'KLEOE20559' is most similar to the commercial *Osteospermum* variety 'KLEO03103' (unpatented). Differences between the varieties are described in Table 2.

TABLE 2

| Comparison with Similar Variety | | |
|---|---|---|
| Characteristic | 'KLEOE20559' | 'KLEO03103' |
| Vigor | Compact | Semi-vigorous |
| Habit | Compact and upright | Semi-upright |

I claim:

1. A new and distinct variety of *Osteospermum* plant designated 'KLEOE20559' as illustrated and described herein.

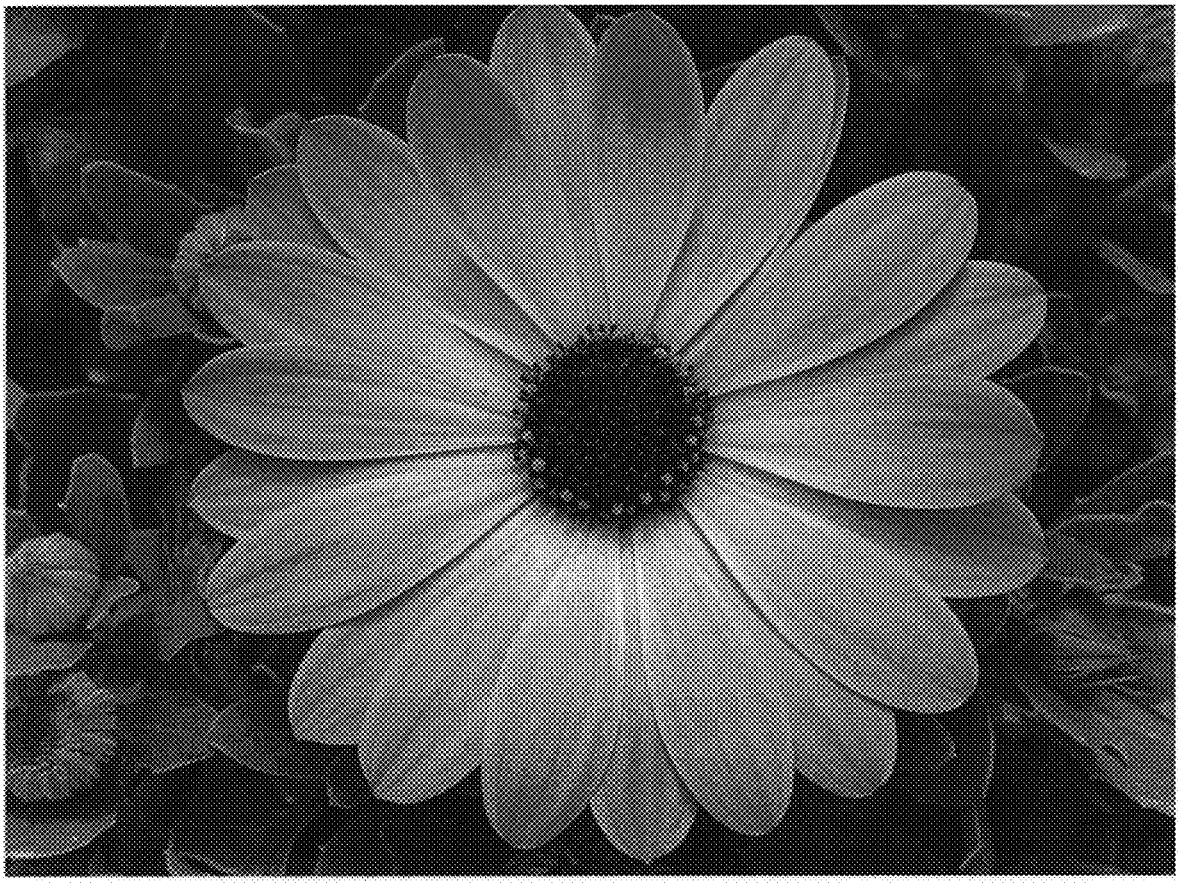

* * * * *